US007574334B2

(12) United States Patent
Tiwari et al.

(10) Patent No.: US 7,574,334 B2
(45) Date of Patent: Aug. 11, 2009

(54) FORMAL METHODS FOR MODELING AND ANALYSIS OF HYBRID SYSTEMS

(75) Inventors: Ashish Tiwari, Los Altos, CA (US); Patrick D. Lincoln, Woodside, CA (US)

(73) Assignee: SRI International, Menlo Park, CA (US)

( * ) Notice: Subject to any disclaimer, the term of this patent is extended or adjusted under 35 U.S.C. 154(b) by 362 days.

(21) Appl. No.: 10/775,419

(22) Filed: Feb. 10, 2004

(65) Prior Publication Data
US 2004/0220786 A1    Nov. 4, 2004

Related U.S. Application Data

(60) Provisional application No. 60/446,964, filed on Feb. 11, 2003.

(51) Int. Cl.
*G06F 17/10*    (2006.01)
(52) U.S. Cl. .................................. 703/2; 716/4; 716/5
(58) Field of Classification Search .................... 703/2, 703/11; 716/4, 5
See application file for complete search history.

(56) References Cited

U.S. PATENT DOCUMENTS

| | | | | |
|---|---|---|---|---|
| 6,957,404 | B2 * | 10/2005 | Geist et al. ..................... | 716/4 |
| 6,983,227 | B1 * | 1/2006 | Thalhammer-Reyero ....... | 703/2 |
| 2003/0033126 | A1 * | 2/2003 | Lincoln et al. ................ | 703/11 |

OTHER PUBLICATIONS

Bultan et al., ACM Transaction 1999, teaches a Model-checking of Concurrent Systems with Unbounded Integer Variable: Symbolic Representations, Approximation, and Experimental Results.*
Hsieh et al., IEEE 1998, teaches a Model abstraction for formal verification.*
Hans Vangheluwe, Multi-Formalism Modelling and Simulation, (2000-2001).*
Wang et al., (Formal Property Verification by Abstraction Refinement with formal, Simulation and Hybrid System Engines, 2001).*
Ashish Tiwari, Formal Methods for Analysis of Hybrid Systems, Stanford University Symposium, Dec. 12, 2001; slideset.
Ashish Tiwari, Formal Methods for Analysis or Hbrid Systems, UC Berkeley Symposium, Feb. 11, 2002, slide set.

(Continued)

*Primary Examiner*—Paul L Rodriguez
*Assistant Examiner*—Andre Pierre Louis

(57) ABSTRACT

A technique based on the use of a quantifier elimination decision procedure for real closed fields and simple theorem proving to construct a series of successively finer qualitative abstractions of hybrid automata is taught. The resulting abstractions are always discrete transition systems which can then be used by any traditional analysis tool. The constructed abstractions are conservative and can be used to establish safety properties of the original system. The technique works on linear and non-linear polynomial hybrid systems: the guards on discrete transitions and the continuous flows in all modes can be specified using arbitrary polynomial expressions over the continuous variables. An exemplar tool in the SAL environment built over the theorem prover PVS is detailed. The technique scales well to large and complex hybrid systems.

5 Claims, 5 Drawing Sheets

OTHER PUBLICATIONS

Ashish Tiwari, et. al. Series of Abstractions for Hybrid Automata, HSCC Conference paper, Mar. 25, 2005 Springer Verlag, LCNS 2289(attached).

Ashish Tiwari, et. al. Series of Abstractions for Hybrid Automata, Mar. 25, 2002, SRI website.

Ashish Tiwari, Series of Abstractions for Hybrid Automata, HSCC slides, Mar. 25, 2002.

Ashish Tiwari et al. Invisble Formal Methods for Embedded Control Systems, SRI website, Aug. 8, 2002.

Ashish Tiwari, Formal Semantics and Analysis Methods for Simulink Stateflow Models, SRI website, Aug. 9, 2002.

Ashish Tiwari, Approximate Reachability for Linear Systems, SRI website, Dec. 10, 2002.

A. Tiwari, P. Lincoln, Automated Technique for Stability Analysis of Delta-Notch Lateral Inhibition Mechanism, SRI web Apr. 18, 2002.

Ashish Tiwari, Abstracting and Model Checking a Hybrid Model of Delta-Notch Cell Differentiation Mechanism,slide presentation, SRI web May 3, 2002.

R. Ghosh,A. Tiwari,C. Tomlin, Automated Symbolic Reachability Analysis with Application to Delta-Notch Signaling Automata, (SRI web Dec. 10, 2002).

Patrick Lincoln; A. Tiwari, Symbolic Systems Biology: Hybrid Modeling and Analysis of Biological Networks, SRI web Jan. 23, 2004.

* cited by examiner

Hybrid Abstraction Applied To Delta Notch

```
g4 = neg AND g6 = neg AND delta = FALSE AND notch = FALSE AND
INV(g0', g1', g2', g3', g4', g5', g6') -->
g6' IN IF g6 = pos THEN IF g3 = pos OR g3 = zero THEN {pos}
    ELSE {pos, zero} ENDIF ELSIF g6 = neg THEN IF g3 = neg OR g3 = zero
                                                    THEN {neg}
    ELSE {neg, zero} ENDIF ELSE IF g3 = pos THEN {pos}
        ELSIF g3 = neg THEN {neg} ELSE {zero} ENDIF ENDIF;
g5' IN IF g5 = pos THEN IF g2 = neg OR g2 = zero THEN {pos}
    ELSE {pos, zero} ENDIF ELSIF g5 = neg THEN IF g2 = pos OR g2 = zero
                                                    THEN {neg}
    ELSE {neg, zero} ENDIF ELSE IF g2 s neg THEN {pos}
        ELSIF g2 = pos THEN {neg} ELSE {zero} ENDIF ENDIF;
g4' IN IF g4 = pos THEN {pos}
    ELSIF g4 = zero THEN {zero} ELSE {neg} ENDIF;
g3' IN IF g3 = pos THEN IF g3 = neg OR g3 = zero THEN {pos}
    ELSE {pos, zero} ENDIF ELSIF g3 = neg THEN IF g3 = pos OR g3 = zero
                                                    THEN {neg}
    ELSE {neg, zero} ENDIF ELSE IF g3 = neg THEN {pos}
        ELSIF g3 = pos THEN {neg} ELSE {zero} ENDIF ENDIF;
g2' IN IF g2 = pos THEN IF g2 = neg OR g2 = zero THEN {pos}
    ELSE {pos, zero} ENDIF ELSIF g2 = neg THEN IF g2 = pos OR g2 = zero
                                                    THEM {neg}
    ELSE {neg, zero} ENDIF ELSE IF g2 = neg THEN {pos}
        ELSIF g2 = pos THEN {neg} ELSE {zero} ENDIF ENDIF;
g1' IN IF g1 = pos THEN IF g2 = pos OR g2 = zero THEN {pos}
    ELSE {pos, zero} ENDIF ELSIF g1 = neg THEN IF g2 = neg OR g2 = zero
                                                    THEM {neg}
    ELSE {neg, zero} ENDIF ELSE IF g2 = pos THEN {pos}
        ELSIF g2 = neg THEN {neg} ELSE {zero} ENDIF ENDIF;
g0' IN IP g0 = pos THEN IF g3 = pos OR g3 = zero THEN {pos}
    ELSE {pos, zero} ENDIF ELSIF g0 = neg THEN IF g3 = neg OR g3 = zero
                                                    THEN {neg}
    ELSE {neg, zero} ENDIF ELSE IF g3 = pos THEN {pos}
ELSIF g3 = neg THEN {neg} ELSE {zero} ENDIF ENDIF
```

Fig 3

A generic plot of data points and Its various approximations

FORMAL METHODS FOR MODELING AND ANALYSIS OF HYBRID SYSTEMS

RELATED APPLICATIONS

This Application is related to and claims priority from provisional application 60/446,964, filed Feb. 11, 2003, the entirety of which is incorporated by this reference.

GOVERNMENT FUNDING

This application was made in part with government support under contract number NAS1-00108 awarded by NASA; this application was also made in part with government support under contract numbers F33615-00-C-3043 and F33615-00C-1700 both awarded by the United States Air Force Research Office and the Defense Advanced Research Project Agency. The Government has certain rights in this invention.

FIELD OF USE

The field of use of the invention is data abstraction, and more particularly data abstraction of hybrid systems.

BACKGROUND

Standard methods for the analysis of hybrid systems rely on numerical techniques for solving the differential equations and can be unsound on certain classes of hybrid systems. These techniques are susceptible to dimension explosion problems as the number of state variables increases. What has been sought is an approach that is both capable of generating sound abstractions and capable of being compositionally applied.

The application of modeling tools to hybrid qualitative and quantitative systems, including, in particular biological systems, poses significant challenges. A means of providing analytical proofs of the unreachability of certain states, as well as stability and bistability properties of complex systems is sought. This capability is outside the reach of traditional modeling for analysis methods.

Further, what is needed is the ability to reason in an automated or semi-automated manner about biological systems to answer complex questions about the biological relevance of complicated molecular or intercellular signaling or other biochemical reaction networks.

SUMMARY OF THE INVENTION

A. Hybrid Modeling

The invention provides for the generation of sound abstractions in every case, and an algorithm according to the invention may be compositionally applied.

HybridAbstraction, the invention taught herein, provides the construction of a series of successively refined, sound abstractions of a hybrid system. The resulting abstracted system is a finite "discrete state transition system" suitable for model checking.

Hybrid systems exhibit both continuous and discrete dynamics. The core algorithm of HybridAbstraction combines qualitative techniques for abstracting the continuous dynamics with predicate abstraction techniques for abstracting the discrete transitions.

Qualitative abstraction consists of keeping only the "sign" information of a finite set of functions or forms over the state variables of the system while ignoring the exact valuations of the state variables. The sign information is updated by recursively keeping track of the signs of the functions representing the derivative of the original functions.

HybridAbstraction Includes:
1. Selecting the seed forms (a set of polynomials);
2. Adding higher order derivatives (or integrals) of the seed forms, using symbolic differentiation (or integration) algorithms;
3. Constructing the abstract system over the abstract state space defined by the 3-valued (i.e. positive, negative, zero) valuation of each of the forms generated by steps 1 and 2 hereinabove. Automation of steps 1, 2 and 3 is accomplished by means of decision procedures, symbolic analysis, and theorem proving.

In step 1, certain functions can be selected as the seed forms. The choice of good seed forms results in better abstractions. This observation is valid for both linear and nonlinear dynamics and all kinds of functions (not necessarily polynomial).

Different sets of seed forms can be chosen for different discrete modes of a hybrid system. In particular, the algorithm described above can be applied compositionally. It can exploit the two kinds of compositions observed in hybrid systems:
  i) A hybrid system is a composition of synchronously executing hybrid automata;
  ii) Each hybrid automation itself is a composition of synchronously executing, continuous dynamical systems.

Thus, not all seed forms are saturated under all continuous dynamics in step 2.

Step 3 of the algorithm preferentially uses fault tolerant theorem proving. Sound procedures (even if incomplete) can be used to construct sound abstractions. In the case where all the seed forms are polynomials and the continuous dynamics are specified using polynomial expressions, then the theorem proving support required to automate the HybridAbstraction algorithm is the quantifier-free theory of reals, which is decidable. The HybridAbstraction algorithm can be applied on other, non-polynomial systems, and on more general seed forms.

B. Biological Systems as Hybrid Models

The inventive method, herein referred to as HybridAbstraction, provides abstraction of a continuous or hybrid model of a biological system to a finite, discrete model. Subjecting the resulting model to discrete reasoning tools and decision procedures enables a desired output. One manner of performing HybridAbstraction includes application of the SAL toolkit (SAL: "Symbolic Analysis Laboratory", an SRI International developed language and toolset for describing and analyzing state transition systems).

Biological systems are described in terms of qualitative or hybrid (qualitative-quantitative) systems. For example, certain phenomena may be described in terms of discrete, non-analogue states: genes are switched on or off; enzymes are active or inactive; protein complex formation is favored or disfavored relative to environmental factors; introns are in or cut out of RNA gene products.

Describing these sorts of biological systems as qualitatively "on/off" fundamentally ignores the multiple modalities of the underlying physical processes—processes which are not simply "on" or "off". Practicing biologists are aware of the hybrid nature of the biological systems.

Computational approaches to biological systems, however, employ strictly quantitative reasoning, where all phenomena are described with exact differential equations describing concentrations of various substances.

The novel HybridAbstraction approach taught herein reconciles the strictly quantitative approach of computational system biology with the qualitative and qualitative/quantitative reasoning brought to bear by the modern practicing biologist. The inventive approach further enables analysis of a system in which many parameters are unknown.

The HybridAbstraction approach includes: a) Describing a biological system in both qualitative and quantitative terms. For example, a gene may be "on" or "off", yet metabolic enzyme reactions may be best described as continuous differential equations. b) Formally describing the property of interest: using descriptions of the property from decidable theories in the system and the property, enabling completely automatic reasoning; c) Carving up infinite possible state space into regions which are not differentiated by the property; d) Applying discrete system analysis tool: including, but not limited to, bounded model checkers, symbolic model checkers, explicit-state model checkers, SAT solvers, term rewriting systems, Knuth-Bendix completion tools, and/or other system analysis tools such as infinite bounded model checking, arithmetic decision procedures, and decision procedures for combined theories; e) Concretizing the result of the application of the discrete system analysis tool to biological system of interest; f) Repeat. The result may further feed the analysis. For example, if a counterexample to the property is found, then the approach includes concretizing the counterexample trajectory back into the continuous domain, as well as providing output or display to the investigator.

HybridAbstraction can both suggest and verify properties of biological subsystems to enable modular reasoning about such subsystems. For example, biology includes many signaling motifs, and many instances of each motif. HybridAbstraction is useful in reasoning about a bistable switch motif, or an oscillator motif, and may enable reasoning about larger biological networks and systems. HybridAbstraction also enables reasoning about potential effects of perturbations to the biological system under investigation. One example of this is gene knock-outs or knock-ins, as well as environmental or drug interaction effects.

C. Chemical Plant Control

HybridAbstraction also provides for modeling chemical processes in petrochemical and other industrial settings. More exact (and provably sound) methods for control of such systems can lead to more optimized performance and productivity. In particular, certain aspects of the chemical reactions underlying industrial processes are known (such as the balanced chemical equations involved), whereas other aspects, such as the dependence of the rate of reaction on continuous variables such as pressure and temperature and partial pressures or concentrations of reactants, products, and various poisons. Seed polynomials can be derived from the known aspects of the system, and the property of interest (such as stability, or optimized generation of target products) formally stated. The present invention provides human designers a better understanding of petrochemical plant operations and status, as well as tools to diagnose anomalous behavior, thereby producing safer and more efficient methods for chemical plant control.

D. Nanoscale Computer Architectures

It is possible to fabricate nanoscale electrical components just a few nanometers in their smallest dimension. For example, silicon nanowires and carbon nanotubes a few atoms (~1 nm) in diameter have been grown in laboratories. Also, single-molecule devices have been fabricated and shown to exhibit diode rectification, negative differential resistance, field-effect gating, and nonvolatile switchable behaviors. Unfortunately, all known nanoscale assembly techniques suffer from high degrees of uncertainty in placement: the individual components may be well characterized, but where the components end up is at least somewhat uncertain. Top-down assembly techniques such as photolithography do not provide the reliable placement of nanometer-scale devices in intentionally designed nanoscale patterns.

D.1 Nanoscale Crossbar

In the particular case of a nanoscale crossbar, which could be used as a digital memory device, or as a PLA-style controller implementing digital logic, a large Cartesian grid of nanoscale wires are formed, perhaps 100 by 100 up to several thousand by several thousand. The vertical wires and horizontal wires may thus cross at between ten thousand and many millions of points. Each crosspoint, however, may only cover an area of several square nanometers (say, 2 nm by 2 nm). In this area may be placed nonvolatile single-molecule nanoscale switches, or the horizontal and/or vertical wires may be assembled with nanoscale FLASH-memory-like floating conductive regions. In any case, each crosspoint is capable of storing approximately one bit of information, where reading and writing that information is performed through precise control of the electrical potential on the horizontal and vertical wires.

Unfortunately, the complete lack of top-down nanoscale assembly techniques, and the uncertainty of bottom-up (chemical) assembly techniques makes it very difficult to predict what the exact electrical characteristics of each switch point might be. Exacerbating the problem are the numbers of switches in electrical contact with each nanowire: uncertainty can thus be compounded a thousand fold.

HybridAbstraction can be advantageously used to perform model-based discovery and configuration of nanoscale computer architectures assembled from nanoscale components. A nanoscale crossbar may be assembled with a high degree of uncertainty in molecular placement at the crosspoints; HybridAbstraction techniques can be used to refine a model of the crosspoint, and thus to enable the reliable use of the crosspoint to store information. For example, the threshold voltage and current which causes reliable switching of nonvolatile switches, and the threshold voltage and current which enables reliable reading of the stored information may not be consistent between crosspoints. HybridAbstraction may be used to discover a model of such a crossbar and to enable the use of that model to configure the nanoscale device. Many nanoscale assembly techniques exist to burn-in or permanently or semi-permanently adjust configuration bits. After a reliable model of a nanoscale memory device is constructed through HybridAbstraction, an automatic system may set these configuration bits to maximize the utility of the device as a digital memory or controller. Thus HybridAbstraction is useful as a configuration tool, perhaps only once after the nanodevice is first manufactured, or perhaps periodically, as the device behavior changes due to random faults or environmental stresses.

D.2 Nanocell

Taking seriously the lack of determined top-down assembly, researchers have developed the concept of a programmable nanocell, which welcomes the uncertainty of initial fabrication, and exploits the reconfigurability aspects of some nanoscale devices in order to construct some digital device of interest. In particular, the nanocell concept contemplates a rectangular well, bordered by between two to several hundred CMOS-lithographic-scale leads, containing tens to hundreds of nanoparticles, randomly bridged by connections often containing nonvolatile switchable molecules. Each nanocell can be viewed as a nanoscale plant, where the connections and the state of those connections must be modeled accurately enough to enable configuring internal connections into a state where the nanocell behaves as some target device of interest (e.g. an adder). The HybridAbstraction can be used to create the necessary model, and seed forms chosen based on the electrical probes attached to the outside of the nanocell well.

D.3 Nanoscale "Trim Bits" Help Push CMOS Limits

As "standard" photolithographic CMOS assembly techniques are pushed to smaller and smaller scales, uncertainty in device performance leads to suboptimal settings of power and clock frequency. HybridAbstraction can be used to determine "trim bits" which might be implemented with nanotechnology nonvolatile switches, placed very near CMOS devices of interest. For example, the tolerances of photolithographic manufacture of a CMOS transistor may not be sufficient to accurately control its threshold voltage, but bottom-up-assembled nanoscale switches sprayed on top of the entire CMOS circuit may be selectively switched to bring the CMOS transistors back within design tolerances. These "trim bits" must be set based on hybrid models of the underlying CMOS devices, and HybridAbstraction may be used to build such models.

E. Molecular Modeling

HybridAbstraction can also be used to model the hybrid continuous and discrete behaviors of electrons in small molecules, and the physical reshaping of molecules such as protein, RNA, and DNA.

E.1 Small Molecule Electrical Characteristics

The precise electrical characteristics of small molecules can be determined experimentally only at very great cost and effort using such techniques as break junctions (where a metal wire is drawn as thin as possible, and then intentionally broken, then a molecule of interest is allowed to assemble bridging that break) and electrically instrumented atomic force microscopes. The computer modeling of electrical properties of small molecules proceeds today with large numerical simulations. HybridAbstraction could be used to model the discrete and continuous aspects of such systems, and to predict properties of interest.

For example, molecules such as 2,5 diethynylphenyl-4-nitroaniline or 2,5-diethynylphenylnitrobenzene have been shown to exhibit very strong negative differential resistance, the unusual property where the resistance falls as voltage is increased. These devices also exhibit switchable states that are retained for long periods of time. These properties can be exploited to create nanoscale computer memories and logic devices. However, the computer modeling of such properties is very difficult and prone to error. Rare examples of qualitative confirmation of computer predictions are far outweighed by incorrect predictions.

HybridAbstraction can be used to model the differential equations governing the movement of electrons around a molecule, and associated physical conformation changes. Classic modeling of molecular systems uses finite element methods and is subject to numerical instability and imprecision. HybridAbstraction can be driven from a given abstract property of interest (ex. electrical conductivity) and an underlying model the governing differential equations, to build an abstract model of the molecule sufficient to address the property of interest.

E.2 Protein Folding

HybridAbstraction techniques can also be applied to help understand the energetically favored physical conformation of large molecules, and the shape of the electrical potential around them. Proteins are assembled as sequences of amino acid residues based on mRNA templates. Once assembled, proteins fold into their energetically favored conformation. In some cases, proteins are folded further by other proteins, and/or subsequently modified post-translation, and/or activated or deactivated (e.g., by phosphorylation). The computational prediction of protein folding is a major challenge.

HybridAbstraction can be used to build models of large protein molecules, and of their external electrical potential. The differential equations governing the interaction between the amino acid residues, and between the folded protein and a given small molecule can be abstracted into simplified form by HybridAbstraction to enable efficient computational predictions of physical properties of those proteins, and the binding of proteins together, and the binding or docking of small molecules with proteins. For example, predicting the behavior of g-protein-coupled receptor proteins is very difficult, because they repeatedly penetrate the cell wall. HybridAbstraction can be used to build a simplified model of a bilipid layer (perhaps as a 2-d fluid), surrounding aqueous envelope, and aspects of the protein conformation can be predicted. Conformation change of g-protein-coupled receptors upon signaling molecule docking can be predicted in a similar fashion.

HybridAbstraction can be applied to other long polymers such as RNA and DNA. The folding of RNA and the excision of introns from RNA sequences can be addressed with HybridAbstraction. The binding of proteins to DNA, and the remodeling of chromatin-DNA complexes can also be modeled with HybridAbstraction techniques.

F. Monitoring and Diagnosis

Abstract models constructed by HybridAbstraction can be used for a variety of applications. Firstly, they can be used to analyze the behavior of the original model. Since the abstract models are discrete and finite-state, formal verification approaches developed for analysis of discrete-state transition systems can be used for their analysis. Secondly, HybridAbstraction can also be used in monitoring and diagnosis of systems, as well as for model validation on such systems. HybridAbstraction can be used to perform model-based monitoring and diagnosis of complex systems that admit hybrid models. For this application, given a hybrid model of the plant and controller, HybridAbstraction is used to create an abstraction by picking the seed forms based on the sensors that are attached to the plant. This abstraction is computed offline. Now, a monitoring and diagnosis system is built by using the sensor readings generated by the system at runtime to make transitions on the abstract model. A fault is detected whenever the monitoring system finds an inconsistency between the actual sensor readings generated by the real system and the possible transitions on the abstraction. Diagnostic information can then be generated by retracing the path on the abstract system.

HybridAbstraction can be used for model validation if the monitoring process described above is moved up in the design cycle for development of the system. More specifically, a monitor, based on an abstraction, is built for the plant model and the actual plant is monitored against this abstract model as described above. Any discrepancies between the actual plant model and the abstract plant model points to inaccuracies in the model. Thus, the model of the plant can be refined and validated using this approach. The design of embedded software, such as controllers, for the plant, is then done over the validated plant model. The crucial aspect of HybridAbstraction as used in these two applications is the fact that the abstract models are much simpler compared to the original models and, hence, they can be executed along with the actual plant (or the actual plant and the controller) in real time.

G. Controller Synthesis

HybridAbstraction provides alternative technology for synthesizing controllers for hybrid plant models. The discrete transition system abstract system generated by HybridAbstraction is amenable to both forward and backward search. Hence, controllers that guarantee desired behavior of the abstract plant model can be synthesized using the standard search based techniques. Controllers synthesized for the abstract models are safe for the actual plant model due to the soundness guarantees provided by the technique.

H. Hybrid Automata

Hybrid systems are modeled as a composition of finitely many hybrid automata. Each hybrid automata is represented in one of two ways:

Standard hybrid automata: A hybrid automata is specified as a finite state automata with continuous dynamics given inside each state (using differential equations).

Inside-out hybrid automata: A hybrid automata is specified using a single specification of the continuous dynamics and complex (If-then-else) expressions for specifying mode changes (that is, updates to continuous and discrete variables).

A combination of these two representations can also be used for representation of hybrid automata. All these styles of specification of hybrid automata and hybrid systems are inter-translatable, but the translated automata are generally too large to be amenable to analysis. The HybridAbstraction technique can construct abstractions directly from these representations, avoiding the translation problems.

BRIEF DESCRIPTION OF THE DRAWINGS

FIG. 3 depicts results of HybridAbstraction applied to a biological system.

DETAILED DESCRIPTION OF THE INVENTION

Introduction

Hybrid systems describe a wide class of systems that exhibit both discrete and continuous behaviors, such as a digital system embedded in an analog environment. Since hybrid systems frequently operate in safety-critical domains, for example, inside automobiles, aircrafts, and chemical plants, analysis techniques are needed to support the design process of embedded software for controlling hybrid systems.

The development of tools and analysis techniques for hybrid systems faces two challenges. It has been shown that checking reachability for very simple class of hybrid systems is undecidable. Several decidable classes have been identified, but all of these classes are too weak to represent hybrid system models that arise in practical applications. In fact, the models of the physical environment in real world scenarios are usually too large and complicated even for analysis tools built on semi-decision procedures and other currently available technologies.

Abstraction is a technique to reduce the complexity of a system design, while preserving some of its relevant behavior, so that the simplified system is more accessible to analysis tools and is still sufficient to establish certain safety properties (those properties that are true of all states). Two powerful abstraction techniques, called predicate abstraction and data abstraction respectively, have been used quite successfully in analyzing discrete transition systems. The invention includes a very simple, yet quite effective, technique based on data abstraction, to construct a series of successively finer abstractions of a given hybrid system.

Hybrid automata are mathematical models for representing hybrid systems. In contrast to discrete transition systems, hybrid automata can make both discrete and continuous transitions and hence, their semantics are given in terms of the states, which are uncountably many, reached over a continuous real time interval. However, the theory of hybrid automata can be given in terms of infinite-state transition systems that contain uncountably many states, but are interpreted over discrete time steps. In HybridAbstraction, the uncountable state space is mapped into a finite state space by the inventive abstraction function. More specifically, the n-dimensional real space $\mathbb{R}^n$ is partitioned into zones that are sign-invariant for all polynomials in some finite set. Increasing the number of polynomials in the set results in finer abstractions.

Significantly, HybridAbstraction extends known qualitative techniques in at least two ways. First, the evolution of arbitrary polynomials (over the state variables) is tracked, and not just the state variables, while constructing an abstraction. Second, whereas qualitative reasoning usually uses the sign of only the first derivative, the invention uses the signs of first $n^{th}$ derivatives. These two non-trivial extensions make HybridAbstraction substantially more powerful.

Figure 1:
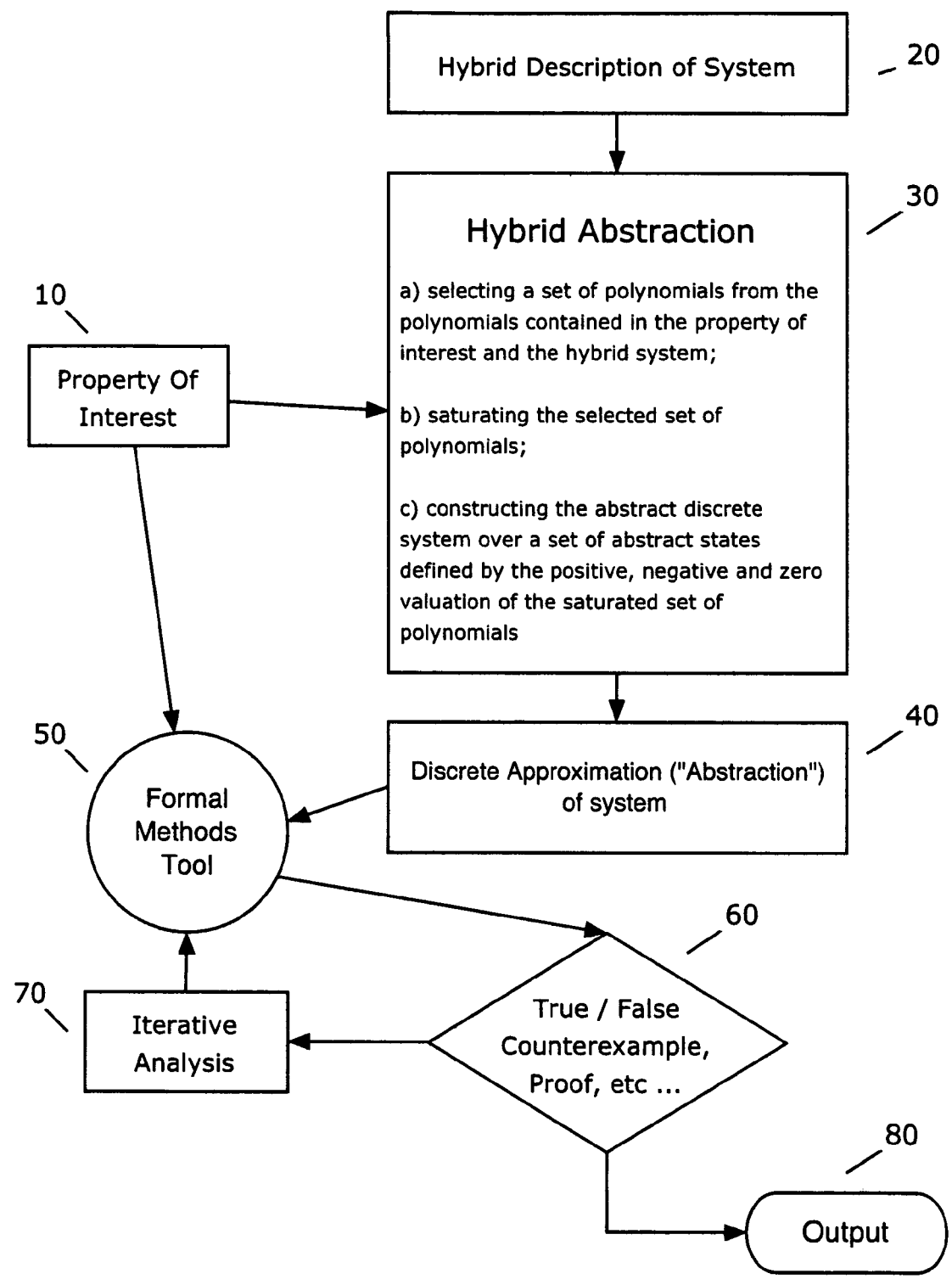
FIG. 1 is illustrative of the use of HybridAbstraction within an analysis framework.

HybridAbstraction as illustrated in FIG. 1 provides for the construction of a series of finer abstractions, enabling an iterative methodology to prove a safety property. Starting with a description of a hybrid system 20 and a property of interest 10, HybridAbstraction 30 creates a first (relatively crude) abstraction 40 (also known as a discrete approximation). A formal methods tool 50 then checks whether the property of interest 10 holds for this abstract system 40. This is represented as a true or false result 60, optionally including a counter example for falsehoods and a proof for truths. If the property of interest 10 is false, the invention provides for the creation of a finer abstraction by an iterative analysis 70 and for checking the property again by formal methods tool 50. This iterative analysis 70 can be repeated until the property is either established or no further refinements of the system can be constructed. Because the resulting abstractions 40 are discrete transition systems, techniques such as model checking can be used as formal methods tool 50. Furthermore, HybridAbstraction is different from many other approaches to hybrid system analysis in that it does not use any numerical methods and techniques.

The process of construction of the abstract system requires logical reasoning in the theory of reals. The first-order theory of real closed fields is known to be decidable. In HybridAbstraction, the first-order theory of reals is used to represent sets of continuous states; HybridAbstraction then uses reasoning over the first order theory of reals for creating abstract transition systems.

Preliminaries

The signature of the first-order theory of reals consists of function symbols $\{+,-,\cdot\}$, constants $\mathbb{R}$, and predicate symbols $\{=,>,\geq,<,\leq\}$. In this theory, the set of terms over a set X of variables corresponds to the set of polynomials $\mathbb{R}[X]$. The set ATM(X), defined as $\{p \sim 0: p \in \mathbb{R}[X]$ and $\sim \in \{=,>,\geq,<,\leq\}\}$, is the set of all atomic formulas. The set WFF(X) of first-order formulas (over X) is defined as the smallest set containing ATM(X) and closed under the boolean operations (conjunction $\wedge$, disjunction $\vee$, implication $\Rightarrow$, and negation $\neg$) and quantification (existential $\exists$ and universal $\forall$). The first-order theory of reals, also denoted by $\mathbb{R}$, is defined as the set of all first-order formulas over the above signature (and a countable set of variables) that are true over the real numbers. The notation $\mathbb{R} \models \phi$ is used to denote the fact that the (first-order) formula $\phi$ is true in the theory of reals. The first-order theory of the real closed fields is a complete theory, i.e., every sentence in WFF(X) is either true or its negation is true in this theory, and the theory is known to be decidable.

Formulas in WFF(X) are denoted by $\phi$, $\psi$, possibly with subscripts, and use p to denote polynomials in the set $\mathbb{R}[X]$. A polynomial p occurs in a formula $\phi$ if there is an atomic formula p~0 in $\phi$. The rest of the notation follows the standard practice in hybrid systems literature.

Continuous Dynamical Systems

For simplicity, hybrid systems with no discrete components are considered in this section, that is, hybrid systems with exactly one mode of operation. A continuous dynamical system CS is a tuple (X, Init, Inv, f) where X is a finite set of variables interpreted over the reals $\mathbb{R}$, $X=\mathbb{R}^X$ is the set of all valuations of the variables X Init$\subseteq$X is the set of initial states, Inv$\subseteq$X is the invariant set of states, and f: X$\mapsto$TX is a vector field that specifies the continuous dynamics. Here TX denotes the tangent space of X. Assume that f satisfies the standard assumptions for existence and uniqueness of solutions to ordinary differential equations. The continuous dynamical systems considered here are autonomous: they have no inputs.

The semantics, $[CS]$, of a continuous dynamical system CS=(X Init, Inv, f) over an interval I=$[\tau_a, \tau_z] \subseteq \mathbb{R}$ is a collection of mappings $\sigma$: I$\mapsto$X satisfying
(a) initial condition: $\sigma(\tau_a) \in$Init,
(b) continuous evolution: for all $\tau \in (\tau_a, \tau_z)$, $\dot{\sigma}(\tau)=f(\sigma(\tau))$, and
(c) invariant: for all $\tau \in [\tau_a, \tau_z]$, $\sigma(\tau) \in$Inv.

In case the interval I is left unspecified, it is assumed to be the interval [0, $\infty$).

Assume that the flow derivative, f, is specified using polynomial expressions over the state variables X, that is $f \in (\mathbb{R}[X])^{|X|}$, where $\mathbb{R}[X]$ denotes the set of polynomials over the indeterminates X and coefficients in $\mathbb{R}$, and |X| denotes the cardinality of X. These polynomials can be nonlinear in general.

EXAMPLE 1

The actuator module in a simple electronic throttle control system is driven by a pulse-width modulated signal and can be described as a hybrid system with two modes:

when the input signal is high, the system is in the "on" mode and is described by $$\dot{V} = \frac{2000}{9}(24 - 2V - I) \qquad \dot{I} = \frac{1000}{15}(120 - 22I)$$

and when the input is low, the system is in "off" mode and is described by $$\dot{V} = \frac{-2000}{3}I \qquad \dot{I} = \frac{2000}{15}(5V - 16I)$$

In each mode, therefore, the actuator behaves as a continuous dynamical system with two continuous variables V and I.

Discrete Transition Systems

A discrete state transition system DS is a tuple (Q, Init, t) where Q is a finite set of variables interpreted over countable domains, Q denotes the (countable) set of all valuations of the variables Q over the respective domains, Init$\subseteq$Q is a set of initial states, and t$\subseteq$Q$\times$Q is a set of transitions. The semantics, $[DS]$, of a discrete state transition system DS=(Q, Init, t) is the collection of all mappings $\theta$: $\mathbb{N} \mapsto$Q satisfying
(a) initial condition: $\theta(0) \in$Init, and
(b) discrete evolution: for all $i \in \mathbb{N}$, ($\theta(i)$, $\theta(i+1)$)$\in$t.

In order to define a notion of abstraction precisely, it is necessary to establish a correspondence between discrete evolutions $\theta$: $\mathbb{N} \mapsto$Q and continuous evolutions $\sigma$: [0, $\infty$) $\mapsto$Q. This is done using discrete sampling.

Definition 1. A discrete evolution $\theta$: $\mathbb{N} \mapsto$Q is a sufficiently complete dis-cretization of a continuous evolution $\sigma$: [0, $\infty$) $\mapsto$Q if there exists a strictly increasing sequence $\mathbb{N}\tau_0, \tau_1, \tau_2 \ldots$) of reals in the interval [0, $\infty$) such that
(i) $\tau_0=0$,
(ii) the function a does not change on the domain ($\tau_i$, $\tau_{i+1}$), that is, a $\sigma(\tau)=\sigma(\tau')$ for all $\tau$, $\tau' \in (\tau, \tau_{i+1})$, and
(iii) for all i, $\theta(2i)=\sigma(\tau_i)$ and $\theta(2i+1)=\sigma(\tau)$, where $\tau_i < \tau < \tau_{i+1}$.

Intuitively, a sufficiently complete discretization captures all the "different" (abstract) states in the given continuous evolution.

Definition 2. Let CS=(X, Init, Inv, f) be a continuous dynamical system and DS=(Q, InitQ, t) be a discrete transition system. DS is an abstraction for CS if there exists a mapping abs: X$\mapsto$Q such that
(a) abs (InitX)$\subseteq$InitQ, and
(b) for every a $\sigma \in [CS]$, if $\sigma'$ is a sufficiently complete discretization of abs($\sigma$), then $\sigma' \in [DS]$.

Here, abs is used to also denote lifting of the function abs to sets and functions. Thus, abs (InitX)={abs(x): x$\in$InitX}. Similarly, if $\sigma$: [0, $\infty$) $\mapsto$X, then (abs($\sigma$))($\tau$)=abs($\sigma(\tau)$). This definition of abstraction corresponds to the usual sense of abstraction, but is applied here to the infinite state transition system associated with a continuous (hybrid) system. The problem of constructing discrete transition system abstractions for continuous dynamical systems in the sense of Definition 2 is considered next. The definition and the procedure for constructing an abstraction naturally extends to hybrid systems, see Hybrid Automata discussion that follows herein.

Abstracting Continuous Dynamical Systems

Data abstraction refers to the idea of using a partition of the domain of interpretation of a discrete system as the new domain of interpretation (in the abstracted system) for the state variables, or expressions over the state variables. The invention includes performing data abstraction on continuous and hybrid systems. Abstract variables are used that represent polynomials over the original continuous variables X and the abstract variables are interpreted over a three valued abstract domain {neg, pos, zero}.

Given a continuous dynamical system CS=(X, InitX, Inv, f), the invention constructs the abstract discrete state transition system DS=(Q, InitQ, t) in two steps. The first phase creates a finite set $P \subseteq \mathbb{R}[X]$ of polynomials over the continuous variables X which are used as the discrete variables Q. In the second phase, the initial states InitQ and the transition relation t are computed.

Phase I: Obtaining a Set of Polynomials

Fixing the set P of polynomials for abstraction involves starting with a small set $P_0$ of polynomials of interest (the "seed forms") and adding to this set the time derivatives of polynomials in $P_0$. The initial set $P_0$ could contain, for example, the polynomials that appear in the statement of the property of interest one wants to establish for the given continuous system, or the polynomials that occur in the guards of mode change transitions. The phase I saturation process involves application of the following inference rule: if p∈P, then add $\dot{p}$, the derivative (with respect to time) of p, to the set P unless $\dot{p}$ is a constant or a constant factor multiple of some existing polynomial in P.

The linear polynomials whose coefficients form a left eigenvector of the A matrix of linear systems should be preferably chosen as seed polynomials for hybrid systems with linear dynamics. In the case of nonlinear systems, suitable seed polynomials are generated using techniques from algebraic geometry. Lyapunov functions are also good choices of seed polynomials.

Because it is assumed that $f \in (\mathbb{R}[X])^{|X|}$, it follows that $\dot{p} \in \mathbb{R}[X]$ is a polynomial. However, note that for general flow derivatives f, specified using arbitrary polynomial expressions, the saturation process might not terminate. But there are special cases where this process is guaranteed to terminate.

Nilpotent Systems. Consider the class of linear time invariant systems specified using a nilpotent matrix A. If X is also used to denote the column vector of state variables X then the flow rate f=AX and hence, $\dot{X}$=AX A polynomial $p=\Sigma_i a_i x_i$ can be written, in matrix notation, as $a^T X$, where $a^T$ denotes the transpose of a. Thus, $\dot{p}=a^T \dot{X}=a^T AX$ and $\ddot{p}=a^T A^2 X$. Hence, if $A^n=0$, then the n-th derivative of the polynomial p is $a^T A^n x=0$. Thus, the saturation process is guaranteed to terminate for such systems.

Systems such that $A^n=rA^m$. If the matrix A used to specify the flow of the continuous dynamical system CS is such that $A^n=rA^m$ for some constant $r \in \mathbb{R}$ and n, $m \in \mathbb{N}$, then again, the saturation process can be shown to terminate. In particular, if $p=a^T X$ is an arbitrary polynomial, then $$\frac{d^n p}{d\tau^n} = a^T A^n X = a^T r A^m X = r \frac{d^m p}{d\tau^m}$$

Because the n-th derivative of p is a constant multiple of the m-th derivative of p, it does not get added to the set P of polynomials in the saturation process. The termination of the saturation process is determined by both the initial set $P_0$ of polynomials and the flow derivative f.

General Case. The inventive abstraction technique works for general (possibly non-linear) time invariant systems whose flow is specified using polynomials. The termination of the saturation phase is not necessary for creating an abstraction. It is possible to stop at any point and pass on the current set P to the second phase. A larger set P yields a finer abstraction as it results in a larger state space in the final abstract system.

EXAMPLE 2

Consider the "off" mode of the actuator in Example 1. Starting with the set $P_0=\{V, I\}$ of polynomials, the phase I saturation procedure first adds the polynomial $\dot{I}=2000/15$ (5V−16I) and then the derivative of this polynomial $\ddot{I}=2000^2/15(-16V/3+77I/5)$. Because the derivative $\dot{V}$ is a constant multiple of the polynomial I∈P, it is not added. Note that the exact derivatives do not need to be added, but only a polynomial up to some constant factor. Although the process of adding derivatives can be continued, this example stops the phase I here with the final set P={V, I, 5V−16I, −80V+231I}.

Phase II: Constructing the Abstract Transitions

Let CS=(X, InitX, Inv, f) be a continuous system and $P \subseteq \mathbb{R}[X]$ be a finite set of polynomials over the set X of variables produced by the first phase. The state variables Q in the corresponding abstract discrete system DS=(Q, InitQ, t) contains exactly one new variable for each polynomial p∈P. Thus, $Q=\{q_p: p \in P\}$. These new variables are interpreted over the domain {pos, neg, zero} and consequently the set Q of all discrete states is the set {pos, neg, zero}$^Q$ of all valuations of the variables Q over this domain. Any such valuation is represented by the corresponding conjunction of atomic formulas. For example, the valuation $\langle q_{p1} \mapsto \text{pos}, q_{p2} \mapsto \text{neg}, q_{p3} \mapsto \text{zero} \rangle$ will be thought of as the formula $p_1 > 0 \wedge p_2 < 0 \wedge p_3 0$. Such conjunctions and valuations are used here interchangeably. The set of all conjunctions representing such valuations will also be denoted by Q. Note that these conjunctions are in the set WFF(X) of formulas over free variables X.

If ψ∈Q is a state in the abstract system DS, represented, for example, as $$\bigwedge_{i \in j_1} p_i > 0 \wedge \bigwedge_{i \in j_2} p_i > 0 \wedge \bigwedge_{i \in j_3} p_i = 0,$$

then the concretization function, γ, maps abstract states to sets of concrete states and is defined by $\gamma(\psi)=\{x \in X: \mathbb{R} \models p_i(x)>0 \forall i \in J_1 \text{ and } \mathbb{R} \models p_i(x)<0 \forall i \in J_2 \text{ and }$ $\mathbb{R} \models p_i(x)=0 \forall i \in J_3\}$ Here, the notation $\mathbb{R} \models p(x)>0$ means that the polynomial p evaluates to a positive number on the point $x \in \mathbb{R}^{|X|}$.

Conversely, if x∈X is a concrete state of the system CS, then the abstraction function, abs, maps a concrete state to an abstract state and is defined by, $$\text{abs}(x) = \bigwedge_{i \in J_1} p_i > 0 \wedge \bigwedge_{i \in J_2} p_i = 0 \wedge \bigwedge_{i \in J_3} p_i < 0$$

where $J_1 \cup J_2 \cup J_3$ is a partition of the set $\{1, 2, \ldots, |P|\}$ such that $i \in J_1$ iff $\mathbb{R} \models p_i(x)>0$, $i \in J_2$ iff $\mathbb{R} \models p_i(x)=0$, $i \in J_3$ iff $\mathbb{R} \models p_i(x)<0$.

The Initial States. Assume that the initial set of states InitX for the continuous system is specified using a first-order formula $\phi_X$ over X. The initial set of states InitQ consists of all valuations ψ of the abstract variables such that the formulas ψ and $\phi_X$ are simultaneously satisfiable.

Specifically,
$$InitQ = \vee\{\psi \in Q: \mathbb{R} \models \exists X: \psi \wedge \phi_X\}.$$

Lemma 1. Let $CS=(X, InitX, Inv, f)$ be a continuous system with the initial states InitX specified by the first-order formula $\phi_X$. If DS, InitQ, and abs are as defined as above, then,
$$abs(InitX) \subseteq InitQ.$$

A formula and the set of valuations it represents are used interchangeably as the context disambiguates the intended meaning.

The Transition Relation. An abstract transition $(\psi_1, \psi_2) \in t$ is added if all of the following conditions hold (for all polynomials $p \in P$):

(a) if $p<0$ is a conjunct in $\psi_1$, then
 (a1) if $\mathbb{R} \models \psi_1 \Rightarrow \dot{p}<0$, then $p<0$ is a conjunct in $\psi_2$;
 (a2) if $\mathbb{R} \models \psi_1 \Rightarrow \dot{p}=0$, then $p<0$ is a conjunct in $\psi_2$;
 (a3) if $\mathbb{R} \models \psi_1 \Rightarrow \dot{p}>0$, then either $p<0$ or $p=0$ is a conjunct in $\psi_2$; and
 (a4) if the valuation of $\dot{p}$ cannot be deduced from $\psi_1$, then either $p<0$ or $p=0$ is a conjunct in $\psi_2$;

(b) if $p=0$ is a conjunct in $\psi_1$, then
 (b1) if $\mathbb{R} \models \psi_1 \Rightarrow \dot{p}<0$, then $p<0$ is a conjunct in $\psi_2$;
 (b2) if $\mathbb{R} \models \psi_1 \Rightarrow \dot{p}=0$, then $p=0$ is a conjunct in $\psi_2$;
 (b3) if $\mathbb{R} \models \psi_1 \Rightarrow \dot{p}>0$, then $p>0$ is a conjunct in $\psi_2$; and
 (b4) if the valuation of $\dot{p}$ cannot be deduced from $\psi_1$ then either $p>0$, $p=0$, or $p<0$ is a conjunct in $\psi_2$;

(c) if $p>0$ is a conjunct in $\psi_1$, then
 (c1) if $\mathbb{R} \models \psi_1 \Rightarrow \dot{p}<0$, then either $p>0$ or $p=0$ is a conjunct in $\psi_2$;
 (c2) if $\mathbb{R} \models \psi_1 \Rightarrow \dot{p}=0$, then $p<0$ is a conjunct in $\psi_2$;
 (c3) if $\mathbb{R} \models \psi_1 \Rightarrow \dot{p}<0$, then $p>0$ is a conjunct in $\psi_2$; and
 (c4) if the valuation of $\dot{p}$ cannot be deduced from $\psi_1$, then either $p>0$ or $p=0$ is a conjunct in $\psi_2$.

This completes the phase of adding transitions to the abstract system. Note that the sign of $\dot{p}$ can be directly read off from $\psi_1$ if $\dot{p}$ was added to P in phase I. If not, then nondeterministic transitions from $\psi_1$ are added assuming all possibilities for the sign of $\dot{p}$. In the final step, this abstract system is refined to eliminate unreachable states and transitions.

Refining the Abstraction. Certain abstract states (and transition to/from those states) can be deleted because either they are infeasible or are explicitly disallowed by the given invariant set Inv of the concrete system. In particular, if the invariant set Inv is specified using a first-order formula $\phi_{Inv}$, then one may delete all abstract states $\psi$ such that $\mathbb{R} \models \exists X: \psi(X) \wedge \phi_{Inv}(X)$. One may also remove all transitions to/from these eliminated abstract states. Note that this process implicitly removes infeasible abstract states, that is, states $\psi(X)$ such that $\mathbb{R} \not\models \exists X: \psi(X)$.

This completes the construction of the abstract system $DS=(Q, InitQ, t)$ for the continuous dynamical system $CS=(X, InitX, Inv, f)$.

Theorem 1. Let $CS=(X, InitX, Inv, f)$ be a continuous system and $DS=(Q, InitQ, t)$, be the discrete abstraction as defined above. Then, DS is an abstraction (Definition 2) for CS.

Even though the abstract transition system is a finite-state system, one need not explicitly represent the states and transitions. The abstract system can be obtained implicitly with the states and transitions specified using predicate formulas.

EXAMPLE 3

Following up on Example 2, the abstract transition system may be constructed on the set $P=\{V, I, 5V-16I, -80V+231I\}$ of polynomials. Assume that the initial abstract state is $I>0 \wedge V>0 \wedge 5V-16I<0 \wedge -80V+231I>0$. (The initial abstract state is obtained from the stable states in the abstract transition system for the "on" mode of the actuator.)

Of the $3^4=81$ abstract states, only 17 are feasible and the infeasible states can be identified using a theorem prover. For example, the state $I=0 \wedge V>0 \wedge 5V-16I<0 \wedge -80V+231I>0$ is infeasible and a decision procedure for the reals can be used to deduce that this formula is unsatisfiable, and can therefore be removed as described earlier to refine the abstraction.

The outgoing transitions from the initial state $I>0 \wedge V>0 \wedge 5V-16I<0 \wedge -80V+231I>0$ are obtained as follows: (a) since $I>0$ and $\dot{I}<0$ (as $5V-16I<0$), in the successor state either $I>0$ or $I=0$, (b) since $V>0$ and $\dot{V}<0$ (as $-I<0$), in the successor state either $V>0$ or $V=0$, (c) since $5V-16I<0$ and $5\dot{V}-16\dot{I}>0$ (as $-80V+231I>0$), in the successor state either $5V-16I<0$ or $5V-16I=0$, and (d) since $-80V+231I>0$ and $-80\dot{V}+231\dot{I}$ is unknown, in the successor state either $-80V+231I>0$ or $-80V+231I=0$. Of the 16 potential successors, only 4 are feasible:

$$I>0 \wedge V>0 \wedge 5V-16I<0 \wedge -80V+231I>0 \quad q_1:$$

$$I>0 \wedge V=0 \wedge 5V-16I<0 \wedge -80V+231I>0 \quad q_2:$$

$$I>0 \wedge V>0 \wedge 5V-16I<0 \wedge -80V+231I=0 \quad q_3:$$

$$I=0 \wedge V=0 \wedge 5V-16I=0 \wedge -80V+231I=0 \quad q_4:$$

Continuing this way, the complete abstract system containing ten reachable abstract states can be constructed. It can also be determined that among these states, only the state $q_4$ is stable.

Hybrid Automata

The technique for constructing finite state abstractions of continuous systems (as described above) extends naturally to hybrid systems.

The abstract system corresponding to the hybrid system $HS=(Q, X, Init, Inv, t, , f)$ and a finite set P of polynomials (over X) is a discrete state transition system $DS=(Q^A, Init^A, t^A)$, where $Q^A=Q \cup (Q_p=\{q_p: p \in P\})$ is the set of discrete variables, $Init^A \subseteq Q^A$ is the initial states, and $t^A \subseteq Q^A \times Q^A$ is the set of transitions. The new discrete variables $Q_p$ are interpreted over the domain {pos, neg, zero} as before. Thus, the set of states in the abstract system $Q^A$ is $Q \times \{pos, neg, zero\}^{Q_P}$ Let $q^a = (q, \phi) \in Q^A$ be a state in the abstract system, where $q \in Q$ is a discrete state of the hybrid automation HS and $\phi$ is a valuation of the variables in $Q_P$ over {pos, neg, zero}. As before, $\phi$ is thought of as a formula in WFF(X). The transitions in the abstract system DS from the state $q^a$ are obtained as a union of two kinds of transitions:

Abstractions of the discrete transitions: If (q, Cond, q') $\in$ t is a discrete transition of the hybrid automata HS, where q, q' $\in$ Q are discrete states and Cond $\subset$ X is a set of continuous states (or the guard) represented by, say, the predicate formula $\phi$ over the variables X, then there is an abstract transition $((q, \phi),(q',\phi)) \in t^a$ if $\mathbb{R} \models \exists X: (\phi(X)) \wedge (\psi(X))$.

Abstractions of the continuous transitions: The rule for constructing new abstract transitions from the continuous flows is the same as before. The first component of the state is left unchanged: a new abstract transition $((q, \phi),(q, \psi))$ in $t^a$ is added if $\psi$ can be obtained from $\phi$ using the rules given above (such rules being applied to the flow corresponding to the discrete state q).

Cases may therefore be handled where the set Q of discrete states in HS is infinite provided that the number of distinct "modes" (each of which can be specified as a formula over Q) are finite.

Theorem 2. Let HS=(Q X Init, Inv, t, f) be a hybrid automata and P∈ℝ[X] be a finite set of polynomials over the set X of real variables. If DS=($Q^A$=Q∪$Q_P$, $Init^a$, $t^a$) is the discrete transition system constructed by the above method, then DS is an abstraction for HS.

The following illustrates the abstraction technique on a simple hybrid system example.

EXAMPLE 4

Consider a thermostat that controls the heating of a room. Assume that the thermostat turns the heater on when the temperature x is between 68 and 70 and it turns the heater off when the temperature is between 80 and 82. Suppose the continuous dynamics in the on and off modes are specified respectively by the equations $$\dot{x}=-x+100 \text{ and } \dot{x}=-x.$$

Assuming that the heater is initially off and the room temperature is between 70 and 80, the hybrid automation is given by HS=(Q, X Init, Inv, t, f), where Q={$q_1$} is the set of discrete variables, Q={on, off} is the set of discrete states (thus, $q_1$ ∈{on, off}), X={$x_1$} is the set of continuous variables, X=ℝ is the set of continuous states, Init={(off,x): 70<x<80} is the initial condition, Inv={(on, x): x<82}∧{(off, x): x>68} is the invariant set, t={(on, x, off): x>80}∪{(off, x, on): x<70} is the set of discrete transitions, and f (on)=−x+100 and f(off)=−x specifies the continuous flow rates.

Now, the set of polynomials that appear in the guards are {x−70, x−80}, and polynomials in the invariant specification are {x−68, x−82}. The derivative of each of these four polynomials is $\dot{x}$. In the mode when the heater is on, this evaluates to −x+100 and in the mode when the heater is off, this is −x. Hence, there are two more polynomials, {x, x−100}, in the set P. Further saturation of the set P of these six polynomials under time derivative yields no new polynomials.

Figure 2:
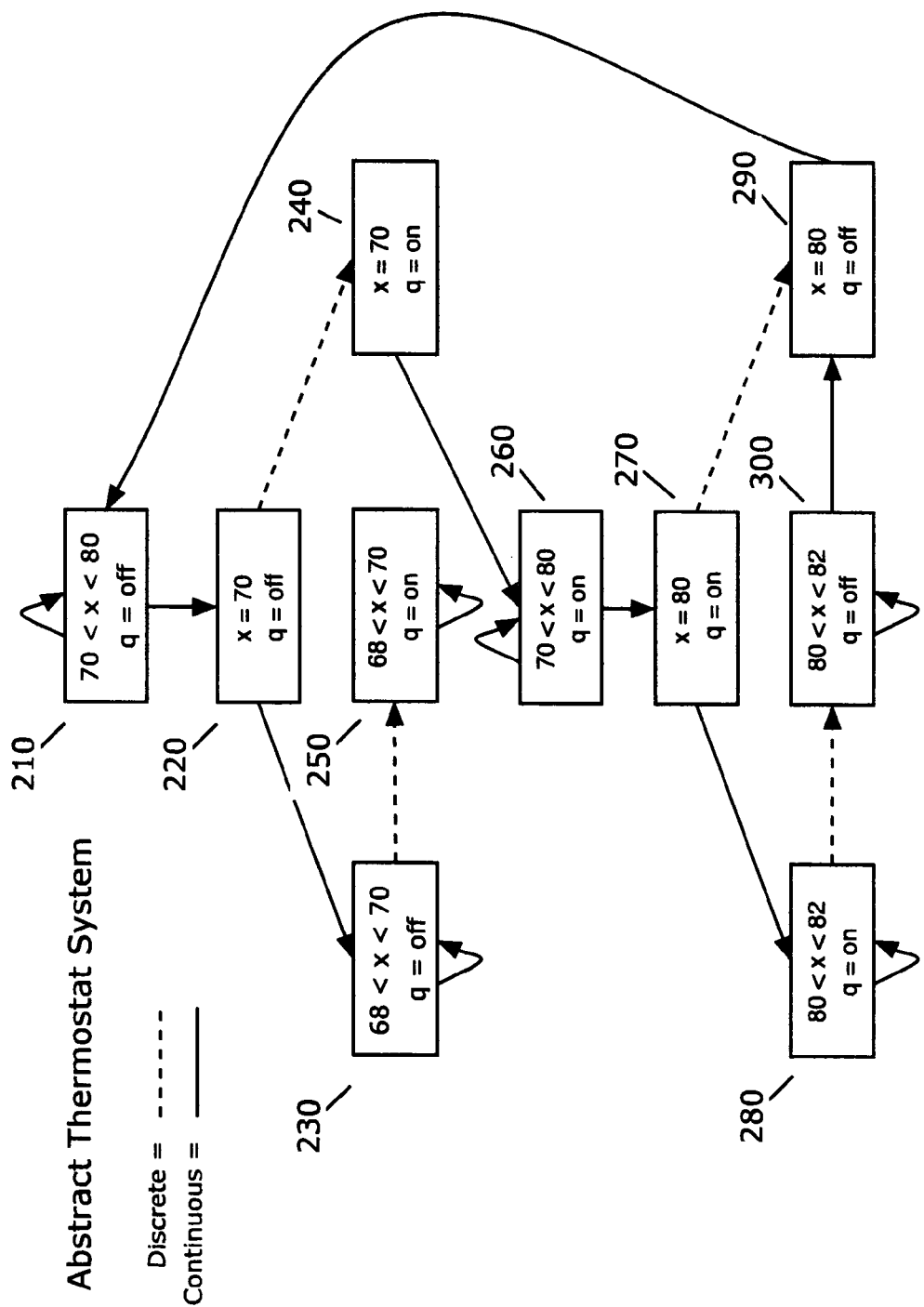
FIG. 2 depicts an abstract thermostat system produced according to the invention.

Using the saturated set P of six polynomials, an abstraction for the thermostat hybrid model can be constructed and the final result is depicted in FIG. 2. In the figure, transitions arising from the continuous and discrete evolutions of H are depicted by dashed lines. Furthermore, the representation of abstract states has been simplified. For example, the expression 70<x<80 denotes the conjunction 70<x∧x<80∧68<∧x<82∧−x+100>0∧x>0. This conjunction is logically equivalent to 70<x∧x<80.

The SAL (Symbolic Analysis Laboratory) tool set provides interfaces that can be used to construct discrete abstractions of hybrid systems as described herein. Other tools known to those in the art may be used for testing, analysis and checking, and this discussion is exemplary, and not to be construed as a limiting. The quantifier elimination decision procedure for the real closed fields is implicitly used to decide the implications over the real numbers. The tool QEPCAD [Quantifier Elimination in elementary algebra and geometry by Partial Cylindrical Algebraic Decomposition], which is built over the symbolic algebra library SACLIB, has been integrated to the theorem prover PVS for this purpose.

The illustrative discrete abstractions constructed do not store information about the duration of a continuous run. However, HybridAbstraction extends, quite easily, to time variant systems by simply explicitly considering time as an other continuous variable. Some timing information can be included in the abstractions if polynomials containing this variable for time are included in the set P.

Qualitative reasoning has been used for modeling and analyzing physical systems in the face of incomplete knowledge of the system dynamics. The idea is to interpret a continuous variable, say x, over an abstract domain of the form {(−∞,$c_0$), $c_0$,($c_0$,$c_1$), $c_1$, ($c_1$,$c_2$), $c_2$, . . . , $c_n$, ($c_n$, ∞)}, where $c_0$, $c_1$, . . . , $c_n$ ∈ℝ are constants. Model construction involves keeping track of the sign of the derivative of x. HybridAbstraction substantially extends qualitative reasoning by allowing for arbitrary polynomials, and not just state variables, for defining the qualitative state space. Additionally, HybridAbstraction includes the use of signs of higher order derivatives in the procedure. The resulting abstractions have more information and are more useful, as they are more amenable to analysis.

Moreover, although the examples of abstractions shown do not retain any timing information apart from the temporal ordering of abstract states, it is known that timing information can be introduced either by treating t as another state variable with time derivative equal to 1, or by incorporating quantitative timing information in the process of constructing an abstraction. See O. Stursberg, et. al. Hybrid Systems IV, vol. 1273 of LNCS, pages 361-377. Springer-Verlag, 1997.

HybridAbstraction is amenable to mechanization. Hybrid-Abstraction has applications to test vector generation for hybrid systems that would cover all regions of the state space, where a region is defined as the subspace which is sign-invariant for a set of polynomials. The invention also provides integration with methods that employ additional quantitative information to create an abstraction.

HybridAbstraction and Biological Systems

Many databases, standard modeling languages, and tools are now becoming available for biological information having to do with network effects. In particular, the Biological Simulation Program for Intra-Cellular Evaluation (BioSPICE) is an open source development movement that is creating computational models, tools, and infrastructure to help deal with modeling and analysis of complex biological systems.

However, despite the exponentially expanding oceans of biological data becoming available, to understand how cells compute and control themselves, accurate models that represent the aspects salient to the questions of biologists are needed. Even relatively simple prokaryotic cells, not to mention more complex eukaryotic (e.g. human) cells, are so complex that the models must be aggressively abstracted to enable more complete, deep, and scalable analysis, and to present results to biological domain experts.

The construction of mathematical models for biological processes is central to the science of bioinformatics and computational biology, but the inherent complexity of biological systems is daunting. Biological processes exhibit dynamics that range over a very wide time scale, contain stochastic components and sometimes discrete components as well. Sigmoidal nonlinearities are commonly observed in biological data correlation and a wide class of such functions is used in the resulting models. Biological processes operate at widely disparate different time and spatial scales, spanning twelve or more orders of magnitude (from single cell to entire organism). A complete model of a biological process is quite complex and poses a challenge for simulation and analysis.

Genetic regulatory networks that work inside a cell form one class of biological system. Such networks are responsible for various kinds of cellular behaviors, for instance, recording, computing, and reacting to changes in the environment. Behavior is controlled through complex interaction between various protein concentrations that are regulated by transcription of various genes, and which, in turn, positively or negatively influence transcription of other genes, thus resulting in complex interwoven networks of control. At a much larger scale, metabolism can be studied at the level of the whole human body. For example, glucose metabolism can be modeled to determine the blood glucose concentration in human tissues. In these cases, a phenomenological model is constructed using tissue and organ level concentrations as basic state variables.

Systems biology explores the quantitative study of biological processes as whole systems instead of isolated parts. Biological subsystems interact with one another to perform sophisticated biological functions, and a systems level view is necessary to understand the complex dynamics that underlie physiology in normal and diseased states. Systems biology research has focused on quantitative stochastic or differential equation models of biological systems.

Mathematical models of biological processes are often constructed by generating equations describing the physical laws that govern the system dynamics. The obtained model is tuned by determining free parameters and unknown rate constants using experimental data. However, this is not always possible, as quantitative experimental data is plagued with high levels of noise, and precise rates of reactions are for the most part unknown to science. Even when some rate constants have been inferred using algorithms for determining minimal error curve fits for available data points, the resulting model is just a "representative" that best matches all the available data.

The actual value of the parameter or rate constant is possibly stochastic in a given range, so there is a danger of overfitting quantitative models to the data, resulting in inaccurate predictions that are highly sensitive to small perturbations in input data. Moreover, the number of different state variables can grow quite large. Too many variables representing different molecular species involved in various compartments can adversely affect the ability to subsequently simulate and analyze the model.

To further complicate matters, assumptions about homogeneity and the presence of large number of molecules often break down at the cellular and cellular compartment levels. This means that mathematical models based on such assumptions cannot be expected to be accurate.

An alternative approach is to seek completely qualitative, rather than quantitative models of biological systems. Some examples of this approach include the high-quality curation and analysis of qualitative metabolic pathway information, symbolic analysis including term rewriting and model checking of curated pathway models, and other logical modeling approaches. However, the focus needn't be on completely logical or symbolic mathematical modeling of biological systems. Hybrid systems may be used as an underlying formalism for modeling and analyzing biological systems. The qualitative or hybrid qualitative-quantitative modeling and analysis of biological systems is referred to as Symbolic Systems Biology.

Biological Hybrid Systems

Hybrid systems, as described earlier, are mathematical models obtained by formally combining continuous dynamical systems with discrete transition systems.

Continuous Dynamics

In a hybrid system, the continuous dynamics of time varying variables are given using differential equations. In models from biology, the differential equations specify how the concentrations of various molecular species evolve over time. These differential equations are obtained using standard physical laws, such as the law of mass action and the law of mass conservation once the gene states are fixed by the discrete logic.

For example, consider the case when a species X reacts (reversibly) with another species Y to form a complex XY. Schematically, this is represented by $$X + Y \underset{k_{-1}}{\overset{k_1}{\rightleftharpoons}} XY$$

where $k_1$ and $k_{-1}$ are the reaction rates for the forward and backward reactions respectively, and the arrow notation $\rightleftharpoons$ is intended to mean reversible reactions.

If x, y, and z denote the concentrations of X, Y, and XY respectively, then using the law of mass action, which states that the rate of a reaction is proportional to the products of the concentrations of the reactants, a system of three differential equations is described:

$$\dot{x} = -k_1 xy + k_{-1} z$$

$$\dot{y} = -k_1 xy + k_{-1} z$$

$$\dot{z} = -k_1 xy - k_{-1} z$$

If a species, say X, participates in more than one reaction, say $$X + Y_i \underset{k_{-i}}{\overset{k_i}{\rightleftharpoons}} XY_i \quad \text{for } j = 1, \ldots, l,$$

then its rate equation is obtained by collecting terms from each reaction in which it participates. Adding a source and a sink term, this becomes $$\dot{x} = \sum_{j=1}^{l} k_j^{-1} z_j - \sum_{j=1}^{l} k_j y_j x + r_{src} - r_{sink}, \qquad \text{Equation 1}$$

where $z_j$ represents the concentration of the complex $XY_j$, $r_{src}$ is the rate of production of X, and $r_{sink}$ is the rate of utilization of X (independent of the reactions that have been accounted for explicitly). For example, if X were a protein, then the effect of the production of X by transcription would contribute a source term and its decay by proteolysis would contribute a sink term.

Figure 4:
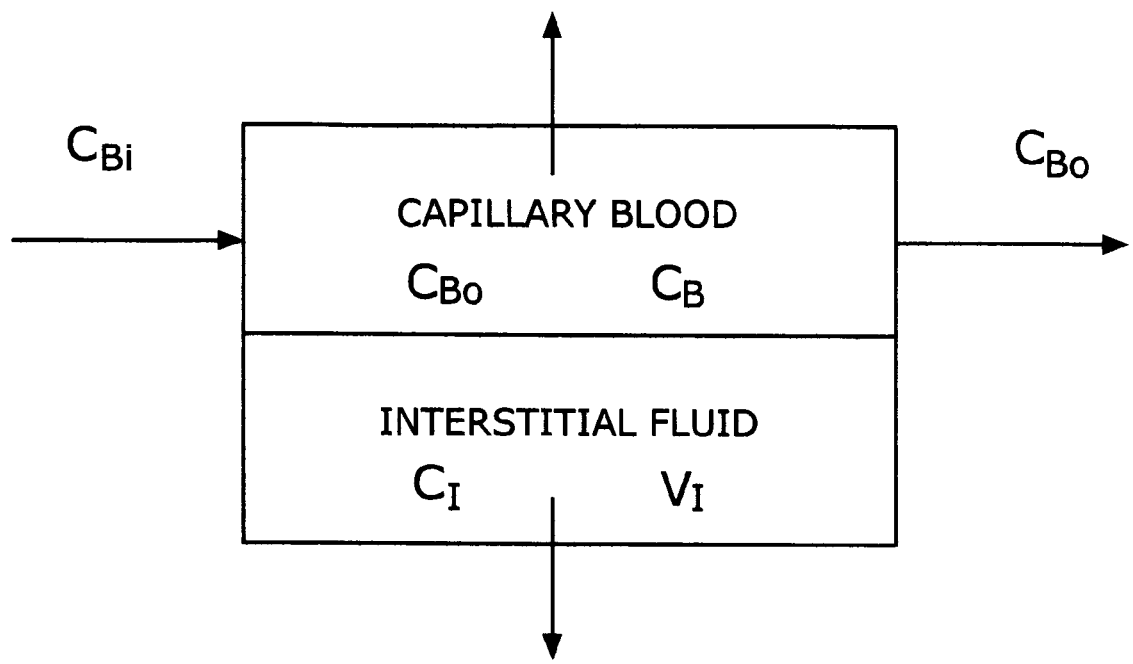
FIG. 4 relates to biological system modeling.

In the example of modeling the blood glucose in human, consider a typical physiologic compartment shown in FIG. 4. The mass balances for this compartment can be written as $$V_B \dot{C}_{Bo} = Q_B(C_{Bi} - C_{Bo}) + PA(C_I - C_{Bo}) - r_{RBC}$$

$$V_I \dot{C}_I = PA(C_{Bo} - C_I) - r_T$$

where $V_B$ is the capillary blood volume, $V_I$ is the interstitial fluid volume, $Q_B$ is the volumetric blood flow rate, PA is the permeability-area product, $C_{Bi}$ is the arterial blood solute concentration, $C_{Bo}$ is the capillary (and venous) blood solute concentration, $C_I$ is the interstitial fluid solute concentration, $r_{RBC}$ is the rate of red blood cell uptake of solute, and $r_T$ is the tissue cellular removal of solute through cell membrane. In the first equation above, the first term on the right-hand side is the effect of convection, the second term corresponds to diffusion, and the last one is the metabolic sink.

Discrete Component

Mathematical models developed by biologists are often continuous dynamical systems, as exemplified by much of the work in systems biology.

It is useful to consider hybrid discrete-continuous models to enable more complete, deep, and scalable analysis. Hybrid modeling and analysis can provide great leverage in the realm of complex biological processes, and can also provide abstractions useful in presenting results to human users. The discrete dynamics can arise in many different ways and a discussion of some of them follows.

Figure 5:
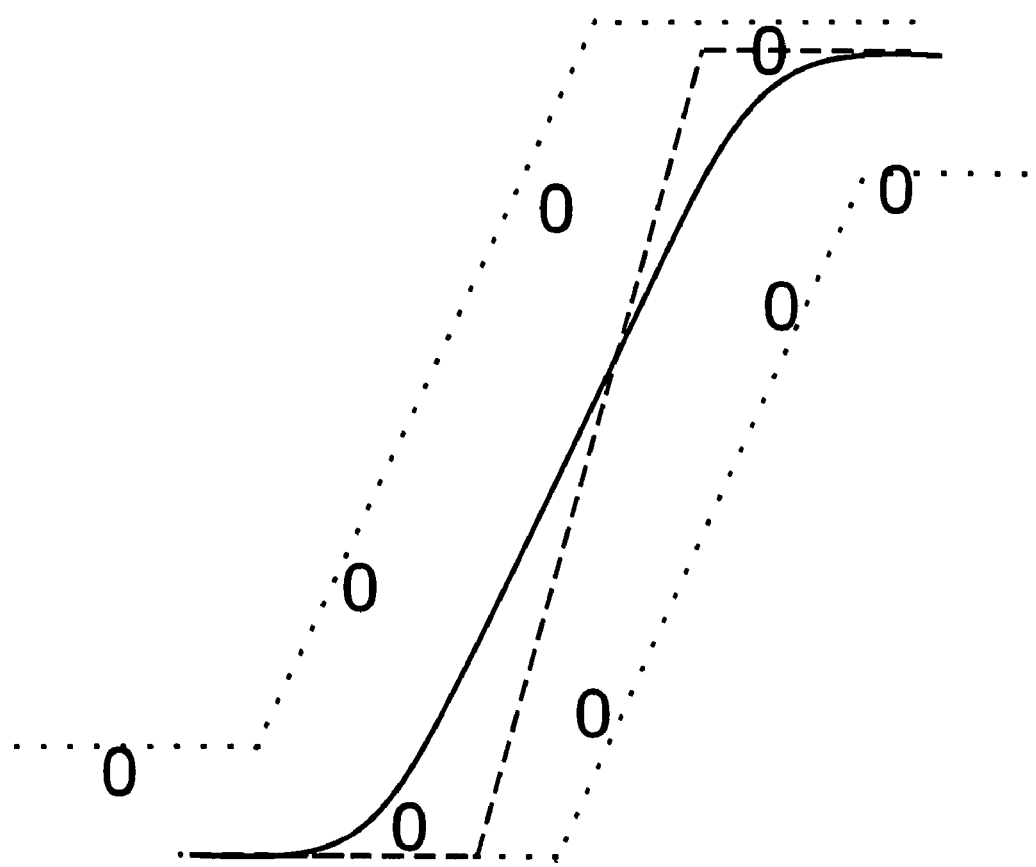
FIG. 5 relates to biological system modeling.

The purely continuous models of biological systems can be too large and complex to be maximally useful for simulation and analysis. On the other hand, a fully discrete approximation of the model can sometimes lose crucial and pertinent information. Hybrid systems provide a rigorous foundation for modeling biological systems at desired levels of abstraction, approximation, and simplification. For example, systems that exhibit multiscale dynamics can be simplified by replacing certain slowly changing variables by their piecewise constant approximation. This is particularly useful when the property of interest is defined on a small time scale. Additionally, sigmoidal nonlinearities are commonly observed in biological data correlation and the corresponding models often use (continuous) sigmoidal functions. These can also be approximated by discrete transitions between piecewise-linear regions. FIG. 5 shows a generic plot of data points and the corresponding sigmoidal curve (solid line) generated by tuning parametric sigmoidal curves. The solid curve is chosen to best match the available data, and the heavy dashed line is a piecewise-linear approximation of the data points. The light dotted lines represent nondeterministic bounds on behavior. In some instances, nondeterministic upper and lower bounds are more useful than deterministic approximations, because they capture all the behaviors of the system.

For example, gene transcription and translation lead to production of proteins in cells. The rate of transcription of the corresponding gene determines the source term in Equation 1 the differential equation for concentration of that protein. This term is, in general, a function of the concentrations of several other molecules that affect the transcription of the relevant gene. This influence of concentrations of proteins and sigma factors on transcription is conventionally modeled using nonlinear continuous functions. This function is usually a steep sigmoidal curve, which is described using higher-order polynomial expressions or hyperbolic trigonometric functions. Sigmoidal nonlinearities are also observed in many other biological data. For instance, in the case of glucose metabolism in human body, the normalized rate of peripheral glucose uptake (a sink term) is such a nonlinear function of the normalized peripheral interstitial insulin concentration.

The use of sigmoidal functions in biological models can be replaced by piecewise constant or piecewise linear approximations as shown by the dashed line in FIG. 5, resulting in a hybrid model with a discrete mode change logic. Such effects are captured via discrete mode changes. A very steep sigmoidal curve can be approximated by a step function. In the gene regulation example, this corresponds to assuming that a particular gene can be in one of two states: "on" or "off". A discrete transition describes how the various regulators combine to choose one of these two states. In completely qualitative modeling, one can represent such states with Boolean variables. More refined but still discrete, stepwise models can result from distinguishing more than two states for genes. For example, "off", "low", "medium" and "high". More complicated discrete logic would then describe the process of choosing between these four possible modes. More accurate approximations for sigmoidal curves are obtained by piecewise linear approximations. These transitions form the discrete component of the hybrid model.

A second source of discrete behavior in models of biological systems is the presence of an inherently discrete process. The physical laws which yield differential equation (continuous) models are applicable only under certain assumptions. For example, the law of mass action holds only when there are large number of molecules which are homogeneously mixed. Certain molecular species are present in plenty and the law of mass action, which states that the rate of a reaction is proportional to the products of the concentrations of the reactants, can be used to describe their evolution using a differential equation. But these assumptions may not be true always. Inside a cell, there are dynamics that are governed by the action of only a few molecules. Ignoring the stochastic aspect temporarily, chemical dynamics at small numbers are best modeled using discrete transitions, cf. the Master equation. This again results in hybrid models of biological processes.

Discrete mode changes can also result from the modeling of faulty modes. In the case of glucose metabolism, the kidney does not excrete any glucose in normal conditions, but it starts excreting glucose if the level of glucose rises very high. This effect can be captured using a discrete transition.

Nondeterminism and Analysis of Safety Properties

Uncertainties and stochastic behavior are common in biology. Rate constants and several other parameters in models of biological systems are determined using algorithms for determining minimal error curve fits for available data points. For example, the rate constants $k_j$ and $k_j$ in Equation 1 and the source and sink terms in that equation are determined in this way. The sigmoidal curve of FIG. 5 is obtained this way from the given data points.

Parameter values thus obtained are "representative" values, they do not capture all observed behaviors. The actual value of the parameter is possibly stochastic in a given range. In many cases, the interest is in knowing about all possible behaviors of the system, rather than the behavior of the system assuming a representative value for the parameters. For example, when studying the effect of insulin injections on blood glucose concentrations, all possible blood glucose concentrations that a human body may exhibit are of interest. In such cases uncertainties can be modeled using nondeterminism and the resulting model can be analyzed for all possible behaviors. In FIG. 5 the given data points lie between the two piecewise-linear curves shown by dotted lines. The nondeterministic hybrid system resulting from using the two dotted lines as the approximation captures all the observed behaviors of the system (and possibly more).

Unknown rate constants can be modeled using unspecified symbolic constants, called parameters, in a hybrid formalism. The rates of reactions and other such unknown constants can be modeled as parameters. Numeric values for such parameters are not required for subsequent analysis. However, to generate nontrivial models that exhibit interesting behaviors, these parameters need to be constrained to take only certain values. Such constraints can be specified in the model using inequalities over expressions containing these parameters. This gives rise to a highly nondeterministic model, that is, the model can exhibit several different behaviors—one corresponding to every exact numerical instantiation for the parameters that is consistent with the constraints. Although this process of nondeterministic modeling does not accurately capture the stochastic nature of biological processes that arises due to random fluctuations on the small numbers of molecules involved, the analysis approach reintroduces some noise by assuming that the unknown parameters are allowed to change randomly (while still remaining consistent with the constraints) finitely many times. To the extent information about exact probabilities remains missing from the non-deterministic model, results of analysis can sometimes be coarse.

Composition

Compositionality is an important feature required to model and analyze large models of any system. Larger systems are described by putting together smaller networks and component subsystems. Compositional modules are subsystems of a larger system that exhibit identifiable interfaces, are modifiable independently, and enable abstract modeling. Modularity is one of the crucial aspects of designing (and describing) large systems, including computer software and hardware systems. It permits clean and scalable description, and also helps appropriately designed tools in performing simulation and analysis on the models.

It is increasingly apparent that biological systems exhibit certain kinds of clean modularity. Biological examples of modular construction include the universal genetic code, translation into amino acid sequences, protein domains, operon structure, bilipid layer membranes, organelles, organs, communities of organisms, and signaling and metabolic pathways. Cells contain many different regulatory pathways, or networks of interacting proteins or other molecules, in several physical compartments, which interact with each other at certain well-defined points. That is, pathways have been identified that have identifiable interfaces with other pathways, appear to be modifiable independently, and enable abstract modeling. The complete behavior of some aspect of a cell can thus be described by putting together all the various models for the individual pathways and sharing the information on molecular species that are shared by two or more such subsystems.

HybridSAL

One approach to modeling is HybridSAL—a system for hybrid system modeling and analysis, embodying the present invention; other approaches known to those of skill in the related arts are also amenable for use in the inventive approach. Models of hybrid systems can be written in the HybridSAL language. These models can then be analyzed for safety properties, that is, properties regarding all possible behaviors of the system. The analysis is done using an abstraction and model checking framework. This tool has been used on examples from a diverse range of application areas such as automobile transmissions, cruise control algorithms, collision avoidance, and genetic and biochemical networks.

HybridSAL can be used to compositionally build parametric hybrid models of biological processes. Three important features that enable effective modeling and analysis of regulatory pathways are the use of (i) discrete transitions to model activation and inhibition of transcription, (ii) parameters to specify unknown reaction rates in the model, with support for specifying constraints on these parameters to capture whatever information is available about the values of these parameters, and (iii) composition to build larger models from component models.

Features such as these distinguish the inventive modeling approach from other currently available approaches.

An automatic tool for simplifying models based on the interest of the biologist renders the model amenable to the HybridSal tool. Complex multiscale and stochastic models of biological processes can be simplified to create smaller hybrid models. This process can be guided by the user. There are several different options for user input. The user can specify the environment and the parts of the model that are irrelevant under the given environment can be sliced. Alternatively, the user can specify the time scale of interest and the dynamics that happen either at very small or very large time scales (compared to what the user has specified) can be replaced by algebraic equations or discrete transitions. As another option, the user can specify the components (compartments) into which the model should be decomposed. The HybridSAL tool can then work on the model thus created by the model simplifier.

Analysis

A modeling formalism is only as useful as the analysis tools that support it. The parametric hybrid modeling formalism enables the development of a variety of analysis tools. Combining discrete and continuous modeling techniques results in simpler and more composable models. Compositionality allows for the development of scalable tools. Parametric modeling languages permit the use of tools for model refinement.

Provided are analysis techniques for:

(a) automatically creating sound approximations of the model that are smaller and simpler, thus amenable to more intensive (computationally complex) analysis, (b) proving properties, such as stability, for the models, (c) generating potentially interesting behaviors of the model, and (d) generating constraints on the unknown parameters automatically so that the constrained model exhibits a certain behavior.

Tools for model refinement, simplification, and simulation, along with improved methods of presenting abstract models and the results of hybrid analysis to biological domain experts are provided.

The process of creating sound abstractions is based on combining qualitative techniques with predicate abstraction. It is powered by powerful symbolic reasoning engines. The simplified model generated is a discrete finite-state transition system. It is an abstraction, in a very precise and rigorous sense, of the original model. The abstraction technique can be further optimized for linear and nonlinear systems. The second step of exploration on this finite-state system is carried out using model-checking.

The kinds of analysis performable on hybrid models of regulatory networks is of interest. Such models are almost always incomplete and under specified. Hence, the analysis process is not a single step activity, but involves interleaved steps of a) model reduction, b) model analysis, and c) model refinement.

Model reduction is the process of simplifying the model based on experimental or domain knowledge, or based on relevance to the particular observation of interest. If interest is in a particular behavior of the organism, then the parts of the model that do not directly influence this behavior can be removed and the resulting simpler model can be used for analysis. This process of model reduction can be done by the user, or by specialized automated tools.

Model analysis consists of analyzing the model for exhibition of given properties. This is presently done in two steps.

In the first step, a qualitative model is automatically extracted from the given parametric hybrid system model. In the second step, the extracted model is analyzed for the properties of interest. The qualitative model is an abstraction, in a very precise formal sense, of the original model. Formally, it is a discrete finite-state transition system. The second step of exploration on this finite-state system is carried out using model-checking.

Model refinement involves concretizing or constraining some of the unspecified parameters. This step is guided in two ways: using the results of the model analysis phase, or using some experimentally observed behavior. In the first case, the model is refined so that the unexpected results returned by the model analysis phase are fixed.

In the second case, given an observed behavior, the parameters of the model are constrained so that the observed behavior becomes a valid behavior of the model and unobserved behaviors are eliminated. One approach for model refinement based on the second approach is described. The well-known approach of counter-example guided abstraction refinement can be used in the first case.

EXAMPLES

Aspects of hybrid modeling and analysis as applied to three specific biological examples are presented. Many other examples will occur to those of skill in the art, and these three are intended as illustrative applications of the inventive method A. Glucose Metabolism in Humans The human glucose-insulin system and the model of this system proposed by Guyton et al. and Sorensen is used as an illustrative example. This model has been used to design a model-based predictive control algorithm to maintain normoglycemia, via a closed-loop insulin infusion pump, in the Type I diabetic patient. A formal correctness analysis of any such control algorithm can be established by showing that blood glucose level remains between 70 and 100 mg/dl always. For "representative" parameter values, this can perhaps be shown using simulations, but that analysis would never yield real guarantees, since parameter values vary over ranges across different individuals. Thus, higher assurance of bounds on behavior requires analysis over all behaviors of the corresponding nondeterministic model. Complete exploration of all behaviors of an abstracted system provides valuable insight beyond the partial exploration of some behaviors (eg. forward simulation) of a more concrete system model.

The final glucose metabolism model consists of twenty-two simultaneous nonlinear ordinary differential equations. It is obtained by dividing the human body into six physiologic compartments: brain, heart and lungs, periphery, gut, liver, and kidney. There is a state variable for the glucose and insulin concentration in each of these six compartments. Wherever necessary, these compartments are subdivided into interstitial fluid space and vascular blood space. This model is decomposed into three components in HybridSal, describing glucose metabolism, insulin metabolism, and glucagon metabolism respectively. Additionally, all nonlinearities in the model arise from sigmoidal functions, which can be eliminated in favor of piecewise linear approximations to yield a hybrid system with linear continuous dynamics. Further simplifications are possible by noticing that the change in glucagon concentrations is very minimal and slow compared to other state variables. The insulin concentrations act as inputs to the glucose module and consequently the insulin concentrations stabilize first, followed by the glucose concentration stabilizing.

There are two sources of insulin in the insulin metabolism model: pancreatic insulin release and insulin injections. If these inputs are set to zero (say, to model a diabetic patient), then the insulin model stabilizes at zero because there is no other source of insulin in the model.

If it is assumed that the inputs to the insulin module change very slowly compared to the dynamics of insulin concentration, then the system can be analyzed assuming constant inputs. The resulting insulin model is a linear system with one complex eigenvalue with negative real part, and all other eigenvalues are real and negative. This indicates that the system is stable, though it could exhibit some damped oscillation. Using the results to compute approximate reachability sets of linear systems, it is easy to compute over-approximations of reach sets for this system. The reach sets enable computation of a bound on the insulin concentrations. The glucose metabolism module reduces to a linear system if the insulin inputs are fixed to their lower or upper bounds. The resulting linear system also has one complex and seven negative real eigenvalues. Again using techniques for the approximate reachability of linear systems, it is possible to compute approximate reach sets that bound the modeled behavior of glucose concentrations. Note that because of the construction of the abstractions and approximations, the bounds thus obtained are conservative and robust to small changes in parameter values.

B. *Subtilis* Sporulation Initiation

The bacteria *Bacillus subtilis* initiates spore formation when there is a nutrient deficiency and the environment is not conducive to growth. The cellular commitment to sporulate is regulated by the complex network of transcriptional control of various genes and interactions between various proteins. Based on the data provided, a model of the sporulation initiation network of *B.Subtilis was* constructed. The HybridSal model consists of six components. The phosphorelay chain is described in one of the important components. The effect of promoters and inhibitors on gene regulation was captured via discrete transitions. Unknown rate constants were modeled using parameters. The parameters were constrained by inequalities. In some cases, the constraints were generated using a tool for doing quantifier-elimination over the theory of reals, called QEPCAD. As noted above, the constrained model is highly nondeterministic and captures a whole spectrum of behaviors.

The constrained parametric hybrid model of the sporulation initiation network was analyzed using Hybrid Abstraction and model checking for stability properties. The stability properties of the resulting hybrid model were observed to be highly sensitive to the discrete logic modeling gene regulation. The HybridAbstraction approach is partly based on qualitative methods. The analysis of the system using these techniques partially accounts for some stochastic behaviors where the unknown parameters are allowed to fluctuate finitely many times to values consistent with the constraints. This results in several unexpected and interesting behaviors of the sporulation model.

C. Delta Notch Lateral Inhibition Mechanism

Inhibitory lateral signaling between adjacent cells (Delta Notch lateral inhibition) is one of the central processes responsible for cell differentiation in a cluster of identical cells. HybridAbstraction was applied to model Delta-Notch inhibition; the basic modeling unit a hybrid automata and more complex models were built using compositions over hybrid automata. Analysis of the model resulting by creation of a finite state discrete abstraction transition system and model checking the abstraction against the property of interest. The completely automated abstraction technique employed suitable decision procedures and theorem-provers. FIG. 3 depicts the abstract SAL transition corresponding to the continuous dynamics in the mode delta=false, notch=false of the Delta-Notch one cell model. A two cell complex may be created by composing two single cells. Because the SAL modeling language name variables occur in two instances of the one cell model, some renaming of variables not local to the module is necessary to avoid conflicts. Similarly, communication between the two cells is captured by renaming variables by the same name.

```
twocells: MODULE
  LOCAL vd1, vd2 IN
    ( (RENAME g4 TO vd2, g5 TO vd1 IN cell)
      [ ]
      (OUTPUT delta2, notch 2 IN
        (RENAME g4 TO vd1, g5 TO vd2,
          delta TO delta2
          notch TO notch2 IN cell )));
```

The composition operator [ ], is used to construct the module "twocells" using two instances of the module "cell." Connecting the output variable g5 of one cell to the input variable g4 of another cell is done by renaming them to the same name. The variables delta2 and notch2 describe the mode of the second cell.

The module "twocells" can be model-checked against the stability properties as in the one cell model. The properties of the two cell model are verified as follows:

```
stability4: THEOREM
    twocells | -
        G ( (delta AND notch - FALSE AND
            delta2 - FALSE AND notch2) -
            G(delta AND notch - FALSE AND
            delta2 - FALSE AND notch2)) ;
stability5 : THEOREM
    twocells | -
        G (( delta - FALSE AND notch AND
            delta2 AND notch2 - FALSE) -
            G(delta - FALSE AND notch AND
                delta2 AND notch2 - FALSE) ) ;
```

This shows that the states where one cell has high Delta and low Notch concentration, while the other has low Delta and high Notch concentration are stable states for a two cell complex. The other states are shown to be unstable, as model-checking the corresponding properties yields a counter-example. However, the property that the two cell system eventually reaches one of the equilibrium states does not hold true, and the model-checker produces a counter-example.

The counter example reveals that the property falsifying trajectory corresponds to an oscillatory behavior of the system. The abstract transition system can be interpreted as exhibiting the sum total of all behaviors of specific concrete realizations of the original system (using specific initialization values and parameter values consistent with the assumptions made during construction of the abstraction). The computational time in creating the abstract and the model checking time was several seconds real clock time.

Symbolic Systems Biology promotes the construction and experimental validation of models and analyses that explain and predict the behavior of biological systems. Symbolic Systems Biology is characterized by a synergistic integration of theory, computation, and experiment.

Only through such an interdisciplinary approach can a scalable, rigorous, and systematic understanding of complex biological processes be achieved. Hybrid discrete-continuous formalisms can be used to provide access to computational analysis enabling accurate modeling of some of the dynamics of biological systems. Together with increasing access to biological network information (through exponentially growing databases and BioSPICE and related tool platforms) and qualitative modeling and analysis techniques, hybrid modeling and analysis of the computation and control of cells, tissues, and organisms may enable Symbolic Systems Biology to be useful to biologists. HybridAbstraction is integral to hybrid modeling and analysis in complex biological systems.

What is claimed is:

1. A computer implemented method for determining the validity of a property of interest with respect to a hybrid system, wherein at least one of the property of interest and a guard of a mode change transition of the hybrid system comprise at least one polynomial, said method comprising the steps of:
   a) abstracting the hybrid system to create an abstract discrete system, wherein abstracting comprises constructing an abstract discrete system over a set of abstract states defined by the positive, negative, and zero valuation of a saturated set of polynomials constructed by saturating an initial set of polynomials selected from the polynomials contained in one or both of the property of interest and the guards of the mode change transitions of the hybrid system, wherein saturating comprises repeatedly choosing a polynomial from the selected set of polynomials and adding a time derivative of the chosen polynomial to the set unless the time derivative is a constant or a constant multiple of a polynomial already in the set;
   b) analyzing, using the computer, the validity of the property of interest with respect to the abstract discrete system; and
   c) outputting the validity of the property of interest on the computer display.

2. The method of claim 1, further comprising:
   d) where the property of interest is invalid with respect to the abstract discrete system, creating a finer abstraction of the hybrid system and analyzing the property of interest with respect to the finer abstraction.

3. The method of claim 1, wherein analyzing the validity of the property of interest is performed by model checking.

4. The method of claim 1, wherein the hybrid system is a model of a biological system.

5. The method of claim 1, wherein the hybrid system is a model of a biological organism.

* * * * *